(12) United States Patent
Kasper et al.

(10) Patent No.: US 7,414,248 B1
(45) Date of Patent: Aug. 19, 2008

(54) ELECTRICAL PENETRATION OF NUCLEAR DETECTOR TUB

(75) Inventors: Robert Kasper, Chicago, IL (US); James Frank Caruba, Bartlett, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 298 days.

(21) Appl. No.: 11/473,695

(22) Filed: Jun. 23, 2006

(51) Int. Cl.
*G01T 1/00* (2006.01)

(52) U.S. Cl. .............................. 250/370.08; 250/363.08; 250/370.09

(58) Field of Classification Search ............ 250/363.03, 250/363.04, 363.08, 363.09, 370.15
See application file for complete search history.

(56) References Cited

U.S. PATENT DOCUMENTS 5,825,031 A * 10/1998 Wong et al. ............ 250/363.03
6,586,744 B1 * 7/2003 Griesmer et al. ........ 250/370.15
6,809,804 B1 * 10/2004 Yount et al. .................... 356/73
7,193,208 B1 * 3/2007 Burr et al. .................... 250/300
2005/0067578 A1 * 3/2005 Ueno et al. ............ 250/370.09
2005/0067579 A1 * 3/2005 Tsuchiya et al. ........ 250/370.15
2007/0297154 A1 * 12/2007 Caruba ........................ 361/760
2008/0035838 A1 * 2/2008 Caruba ........................ 250/250

* cited by examiner

*Primary Examiner*—David P. Porta
*Assistant Examiner*—Mark R Gaworecki
(74) *Attorney, Agent, or Firm*—Peter L. Kendall (57) ABSTRACT

Systems, methods and apparatus including an electrical penetration assembly for coupling a plurality of photo-multiplier tubes (PMTs) inside of a tub enclosure of a nuclear detector with an acquisition electronics system (AES) outside of the tub enclosure. The electrical penetration assembly may include at least one flex circuit, a plurality of flex circuit-PMT connectors, at least one flex circuit-AES connector, a flex circuit guide, a tub-penetration mechanical support, a support-to-tub retention mechanism, and a light seal.

20 Claims, 11 Drawing Sheets

ELECTRICAL PENETRATION OF NUCLEAR DETECTOR TUB

BACKGROUND

1. Field of Invention

The present invention generally relates to an apparatus and method for electrical penetration of a nuclear detector tub, and in particular, electrical penetration along the axial or transaxial planes. Moreover, such electrical penetration may provide an integrated seal against visible light (light seal).

2. Description of Related Art

There are several distinctive types of imaging systems in contemporary nuclear medicine. One type may employ gamma scintillation cameras (GSCs), so-called "position sensitive" continuous-area detectors, or simply, nuclear detectors. An exemplary GSC is a single photon emission computed tomography (SPECT) scanner. Another type of imaging system involves computed tomography ("CT") of X-ray imaging. By comparison, magnetic resonance imaging (MRI), formerly referred to as magnetic resonance tomography (MRT) or nuclear magnetic resonance (NMR), is a method used to visualize the inside of living organisms relying on the relaxation properties of excited hydrogen nuclei in water placed in a powerful, uniform magnetic field.

Insofar as each imaging system has it own advantages and disadvantages, clinics may have several different systems, possibly in proximity to each other. The closer the proximity of the systems, the greater the potential that exists that one system may interfere with another. The likelihood of a system interfering with another system depends in large part on the types of imaging technology involved and the sensitivity of the interfered-with system to the imaging technology of the interfering system. For instance, a CT scanner uses an active detection technology involving high-energy X-rays that easily may interfere with a GSC, which uses a passive-detection technology sensitive to low energy densities. While measures are taken, therefore, to effectively shield a GSC from interference from a CT scanner, these measures themselves may raise new challenges.

X-rays are a form of electromagnetic radiation with a wavelength in the range of 10 to 0.1 nanometers, corresponding to frequencies in the range 30 to 3000 PHz ($10^{15}$ hertz). X-rays are primarily used for diagnostic medical imaging and crystallography. X-rays are a form of ionizing radiation and as such can be dangerous. Electromagnetic waves with a wavelength approximately longer than 0.1 nm are called soft X-rays. At wavelengths shorter than this, they are called hard X-rays.

The basic production of X-rays is by accelerating electrons in order to collide with a metal target (copper, molybdenum or tungsten usually). Here the electrons suddenly decelerate upon colliding with the metal target and if enough energy is contained within the electron it is able to knock out an electron from the inner shell of the metal atom and as a result electrons from higher energy levels then fill up the vacancy and X-ray photons are emitted. This causes the spectral line part of the wavelength distribution. There is also a continuum bremsstrahlung component given off by the electrons as they are scattered by the strong electric field near the high Z (proton number) nuclei.

Computed tomography (CT), originally known as computed axial tomography (CAT or CAT scan) and body section roentgenography, is a medical imaging method employing tomography where digital geometry processing is used to generate a three-dimensional image of the internals of an object from a large series of two-dimensional X-ray images taken around a single axis of rotation. The word "tomography" is derived from the Greek tomos (slice) and graphia (describing). Computed tomography systems generate an infinite set of X-ray beam projections through an object to be examined.

CT systems subject the object under examination to one or more pencil-like X-ray beams from many directions. The X-ray beams passing through the object are attenuated by various amounts, depending upon the nature of the object traversed (e.g., bone, tissue, metal, etc.). One or more X-ray detectors, disposed on the far side of the object, receive these beams and provide analog output signals proportional to the strength of the incoming X-rays. Each detector output is then digitized and computer processed to help produce an image of a slice of the object.

The resultant detected X-ray data are computer processed to reconstruct a tomographic image-slice of the object. CT produces a volume of data which can be manipulated, through a process known as windowing, in order to demonstrate various structures based on their ability to block the x-ray beam. Although historically the images generated were in the axial or transverse plane (orthogonal to the long axis of the body), modern scanners allow this volume of data to be reformatted in various planes or even as volumetric (3 D) representations of structures.

Hard X-rays overlap the range of "long"-wavelength (lower energy) gamma rays, however the distinction between the two terms depends on the source of the radiation, not its wavelength: X-ray photons are generated by energetic electron processes, gamma rays by transitions within atomic nuclei. It is important to note that there is no physical difference between gamma rays and X-rays of the same energy—they are two names for the same electromagnetic radiation. Rather, gamma rays are distinguished from X-rays by their origin.

Gamma rays (often denoted by the Greek letter gamma, $\gamma$) are an energetic form of electromagnetic radiation produced by radioactive decay or other nuclear or subatomic processes such as electron-positron annihilation. Gamma rays form the highest-energy end of the electromagnetic spectrum. They are often defined to begin at an energy of 10 keV, a frequency of 2.42 EHz, or a wavelength of 124 pm, although electromagnetic radiation from around 10 keV to several hundred keV is also referred to as hard X-rays.

Gamma scintillation cameras, GSCs, are primarily used to measure gamma events produced by very low-level radioactive materials (called radionuclides or radio-pharmaceuticals) that have been ingested by, or injected into, a patient. The signals from the GSCs are used to generate images of the anatomy of organs, bones or tissues of the body and/or to determine whether an organ is functioning properly. The radiopharmaceuticals are specially formulated to collect temporarily in a certain part of the body to be studied, such as the patient's heart or brain. Once the radio-pharmaceuticals reach the intended organ, they emit gamma rays that are then detected and measured by the GSCs. Nuclear detectors perform spectroscopy and event X/Y positioning by processing signals from a constellation of Photo-multiplier Tubes (PMTs). The current HD series detectors contain 59 PMTs.

While it may be convenient for a clinic to have a GSC system in proximity to a CT system, a significant problem may arise when this is done. In particular, if any X-rays of significant magnitude from the CT system infiltrate the GSC, the output of the GSC at best will be skewed. Indeed, a GSC includes a large area scintillation crystal, which functions as a gamma ray detector and is typically sodium iodide doped with a trace of thallium (NaI(Tl)). The crystal converts high-energy photons (e.g.; gamma rays and X-rays) into lower energy photons, i.e., visible light. The relatively high, and constant, energy profile of X-ray events (as compared with gamma ray events) will likely drive the crystal significantly more than would gamma rays, thereby skewing the detection function of the GSC. More likely, the relatively sensitive photochemistry of the scintillation crystal will be over driven by the X-rays and may take a very long time (sometimes hours) to settle and again become useful in measuring gamma rays. At worst, the crystal may be permanently damaged from excessive levels of X-ray radiation.

To guard against the deleterious effects of stray X-rays blinding the scintillation crystal and the PMTs and possibly frying the associated electronics, a GSC has a lead enclosure, i.e., tub, to block the stray X-rays. Furthermore, because the scintillation crystal emits faint amounts of light upon scintillation, the interior of the GSC must be shielded from ambient light that would blind the photosensors in the GSC used to measure the scintillation light emissions.

Due to the large number of interconnections between PMT preamplifiers and an acquisition electronics system, portions of the acquisition electronics system have been packaged inside the tub. The cables that historically did exit the tub from the interior portion of the acquisition electronics system required light seals, for which a compliant packable material was used, making the seals difficult to handle, not integrated with the tub, and non-reusable. Because these connections generate heat, a significant amount of heat accumulates in the tub, detrimentally affecting the GSC's reliability. Likewise, the connections involve numerous printed circuit boards (PCBs) and cables, which must be disassembled to access a PMT needing replacement, making the GSC hard to service. Similarly, because the detectors need to be built in test stands, disassembled and then reassembled in the tubs, this arrangement of the connections compounds the effort needed to manufacture the GSCs.

While this arrangement has been functional, reliability, serviceability and manufacturability would all benefit if the electronics could be relocated outside of the tub. For these electronics to be placed outside the tub, an electrical penetration of tub must support all of the PMT interconnections, including High Voltage PMT & dynode bias, and provide a light seal. Moreover, an electrical penetration should facilitate easy assembly & disassembly, which are important for manufacturing and service.

Accordingly, there is a need in the art for new methods and apparatus for enabling relocation of the electronics outside of the tub of a CGS.

BRIEF SUMMARY OF THE INVENTION

In accordance with one or more embodiments of the present invention, a method of assembling a tub of a nuclear detector may include connecting interconnection circuitry to PMTs, penetrating the tub with the interconnection circuitry, and securing the interconnection circuitry to the tub where the interconnection circuitry penetrates the tub.

In accordance with one or more other embodiments of the present invention, a method of coupling a plurality of PMTs inside of a tub with an acquisition electronics system outside of the tub may include providing an electrical penetration assembly between the plurality of PMTs and the acquisition electronics system.

Providing the electrical penetration assembly may include connecting flex circuit-PMT connectors to the plurality of PMTs, penetrating the tub with the flex circuits; and connecting the flex circuit-AES connectors to the acquisition electronics system. Providing the electrical penetration assembly also may include guiding the interconnection circuitry through the tub at a location of penetration, and supporting the interconnection circuitry at the location of penetration. Providing the electrical penetration assembly furthermore may include sealing out light from the tub enclosure at the location of penetration of the tub enclosure, and dielectrically insulating the location of penetration.

In accordance with one or more additional embodiments of the present invention, an apparatus may comprise an electrical penetration assembly for use with a tub enclosure of a nuclear detector, wherein: the tub enclosure encases a plurality of photo-multiplier tubes (PMTs); an acquisition electronics system (AES) resides outside the tub enclosure; the electrical penetration assembly provides electrical interconnections between the plurality of PMTs and the acquisition electronics system; and, the electrical interconnections penetrate the tub enclosure. The nuclear detector may comprise a single photon emission computed tomography (SPECT) scanner. The electrical penetration assembly may comprise a tub-penetration mechanical support, a support-to-tub retention mechanism, and a light seal. The electrical penetration assembly further may comprise at least one flex circuit, a plurality of flex circuit-PMT connectors, and a flex circuit guide. The electrical penetration assembly additionally may comprise at least one flex circuit-AES connector.

In accordance with one or more embodiments of the present invention, a nuclear detector system may include a plurality of photo-multiplier tubes, a tub enclosure encasing the plurality of PMTs, an acquisition electronics system residing outside the tub enclosure, interconnection circuitry coupling the plurality of PMTs with the acquisition electronics system, and an electrical penetration assembly. The electrical penetration assembly may penetrate the tub enclosure with the interconnection circuitry and electrically connect the interconnection circuitry to the plurality of PMTs. The electrical penetration assembly may comprise a tub-penetration mechanical support, a support-to-tub retention mechanism, and a light seal. The electrical penetration assembly further may comprise at least one flex circuit, a plurality of flex circuit-PMT connectors, and a flex circuit guide. The electrical penetration assembly additionally may comprise at least one flex circuit-AES connector.

In accordance with one or more other embodiments of the present invention, an apparatus may comprise means for electrically connecting a plurality of photo-multiplier tubes inside of a tub enclosure of a nuclear detector and an acquisition electronics system outside of the tub enclosure; and means for penetrating the tub enclosure with the interconnection circuitry. The means for electrically connecting may include means for electrically interconnecting the plurality of PMTs. The means for electrically interconnecting the plurality of PMTs may include a high-density configuration of interconnection circuitry. The apparatus may further comprise means for sealing out light, wherein the means for sealing out light prevents light from entering the tub enclosure where the interconnection circuitry penetrates the tub enclosure. The apparatus may further comprise means for mechanically supporting the means for penetrating the tub enclosure with the interconnection circuitry. The apparatus may further comprise means for dielectrically insulating the means for electrically connecting a plurality of PMTs.

Other aspects, features, advantages, etc. will become apparent to one skilled in the art when the description of the exemplary embodiments of the invention herein is taken in conjunction with the accompanying drawings.

BRIEF DESCRIPTION OF THE DRAWINGS

For the purposes of illustrating the various aspects of the invention, there are shown in the drawings forms that are merely exemplary, it being understood, however, that the invention is not limited to the precise arrangements and instrumentalities shown. In the drawings, like numerals indicate like elements.

DETAILED DESCRIPTION OF EXEMPLARY EMBODIMENTS

Figure 1:
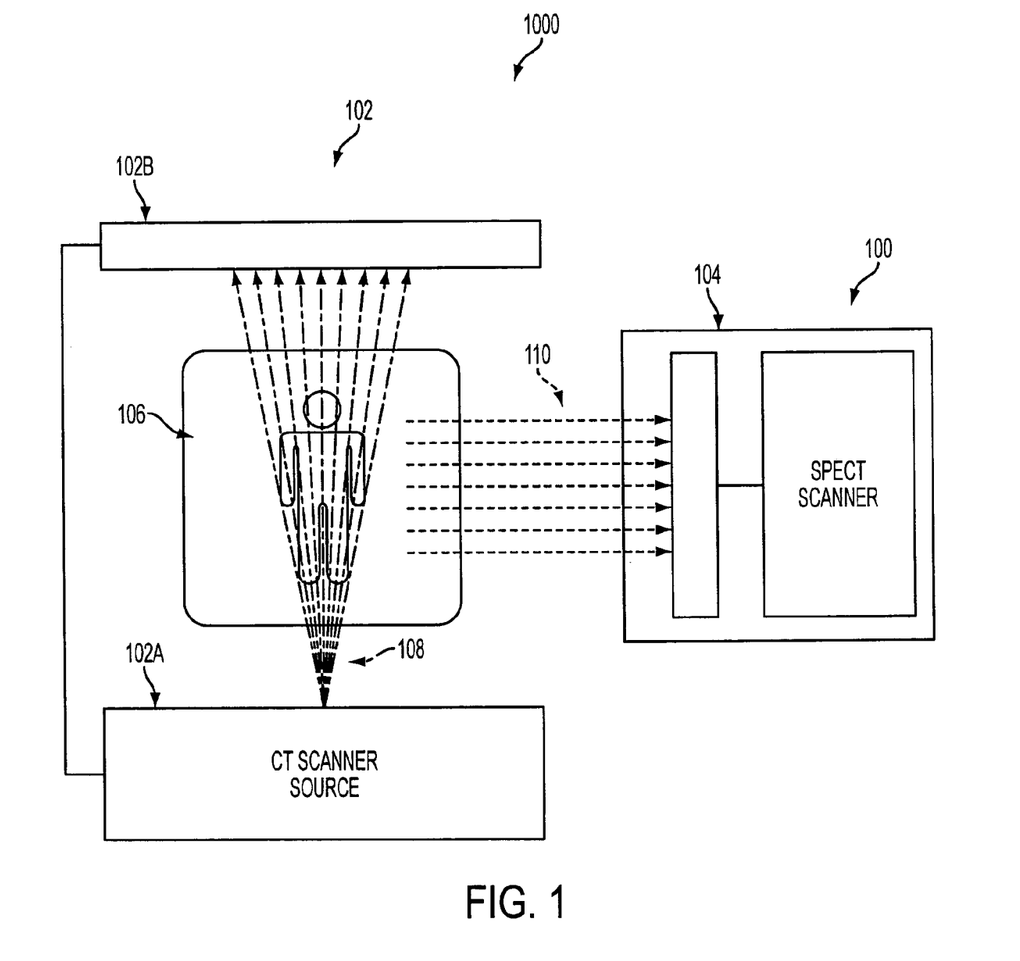
FIG. 1 is a block diagram of a clinic setting having in close proximity a SPECT scanner and a CT scanner in accordance with one or more embodiments of the present invention.

Referring to FIG. 1, a block diagram depicts a clinical setting 1000 having in close proximity a SPECT scanning system with a CT scanning system. The clinic setting 1000 includes a nuclear detector 100, such as a SPECT scanner, and a CT scanner 102 that operate to provide images of the anatomy of a patient 106. While the present invention relates primarily to improvements to the configuration of the nuclear detector 100, the CT scanner 102 is presented to provide a context in which shielding of the nuclear detector 100 is required. It should be noted that shielding is provided for patients being imaged, patients walking around the area with radionuclides in their body, and to compensate for the flux density of the CT.

The CT scanner 102 includes a CT scanner source 102A (of X-rays 108) and a detection array 102B located generally diametrically opposite to the CT scanner source 102A with the patient 106 therebetween. The detection array 102B is responsive to X-rays 108 emanating from the CT scanner source 102A and passing through the patient 106. The SPECT scanner 100 includes gamma ray detection circuitry and post processing circuitry that will be discussed in more detail hereinbelow. The SPECT scanner 100 is responsive the gamma rays 110 emanating from radionuclides within the patient 106.

While the SPECT scanner 100 is designed to measure gamma rays, the CT scanner 102 is designed to measure X-rays. In particular, the CT scanner 102 generates an infinite set of X-ray beam projections 108 through the anatomy of the patient 106. The resultant detected X-ray data are computer processed to reconstruct a tomographic image-slice of the anatomy. The CT scanner source 102A generates an X-ray electron beam 108 that scans in an arc-like shape through the patient 106 to the detector array 102B. The detector array 102B may include a relatively large number of detectors (perhaps 2,000-5,000) that sequentially receive at least a portion of the moving beam of X-rays 108. Each detector produces an analog output signal (typically a few nA of current) that is subject to a current-to-voltage conversion to yield an analog signal of perhaps several hundred mV. The analog detector outputs are then digitalized using analog to digital ("A/D") converters. Post processing circuitry of the CT scanner 102 computes the tomographic image-slice of the anatomy from the digitized signals.

Further details regarding the basic operation and structure of the CT scanner 102 may be found in U.S. Pat. No. 5,448,609, the entire disclosure of which is hereby incorporated by reference.

As discussed above, the CT scanner source 102A presents a potential hazard to the SPECT scanner 100 inasmuch as stray X-rays therefrom may stun (or damage) the gamma ray detection circuitry of the SPECT scanner 100. Thus, the SPECT scanner 100 has a lead tub enclosure 104. The tub 104 seals out stray radiation 108, but also seals out ambient light that would be detrimental to the photosensitivity of the SPECT scanner 100. The tub 104 may be made of lead or any other material that effectively blocks X-rays.

Figure 2:
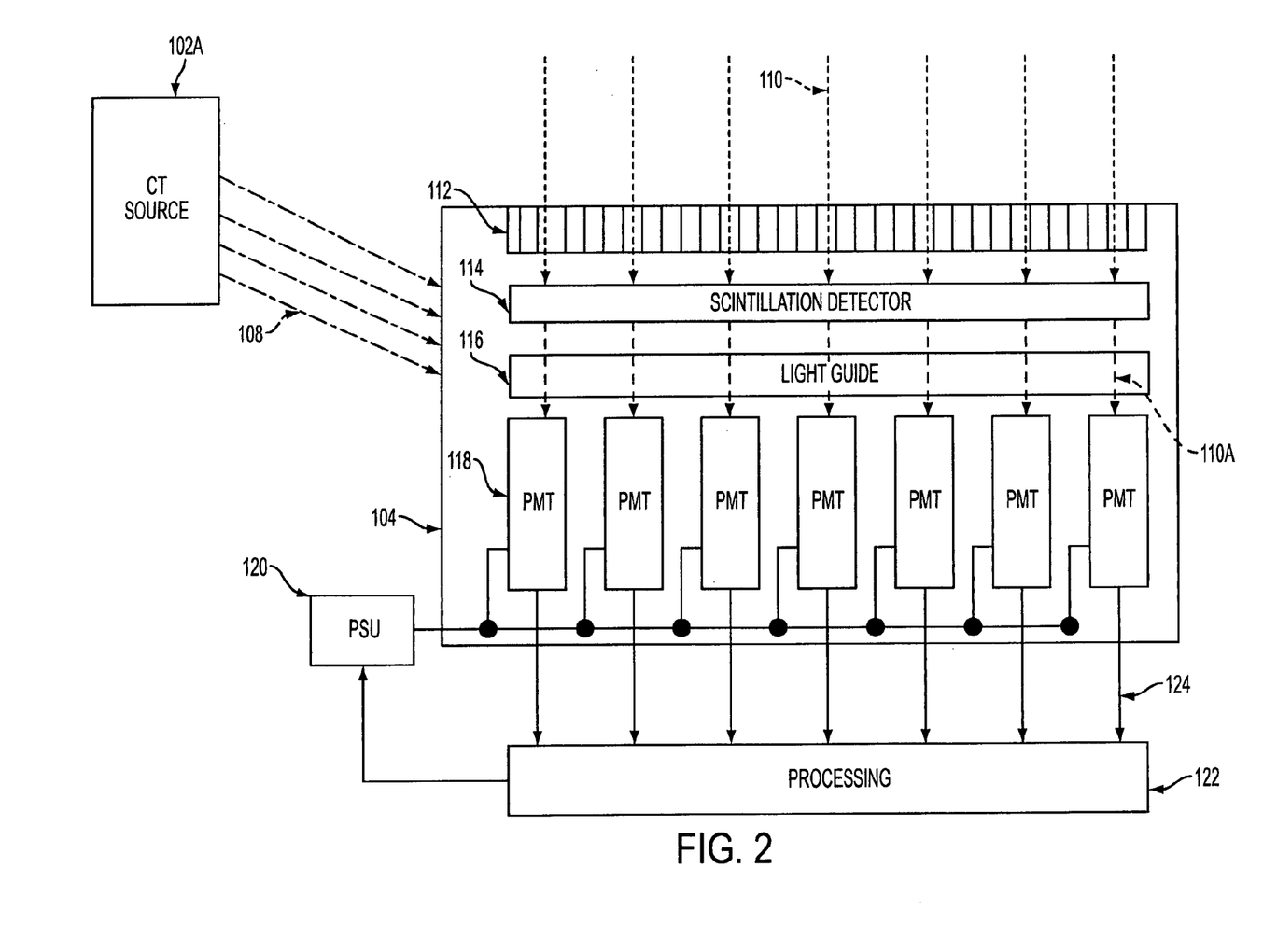
FIG. 2 is a more detailed block diagram primarily of the gamma ray detection circuitry of the SPECT scanner of FIG. 1 in accordance with one or more embodiments of the present invention.

Referring to FIG. 2, a more detailed block diagram primarily depicts a gamma ray detection circuit of the SPECT scanner 100. Portions of the gamma ray detection circuitry are similar to those of U.S. Pat. No. 3,011,057 (to Anger), the entire disclosure of which is incorporated by reference herein. In particular, the gamma ray detection circuit includes a parallel hole collimator 112, a scintillation detector (crystal) 114, a light guide 116, a plurality of photo multiplier tubes (PMTs) 118, a high voltage power supply 120 for the PMTs 118, and an acquisition electronics system 122 for processing of the data from the PMTs 118. Interconnection circuitry 124 is used to connect the PMTs 118 to the power supply 120 and the acquisition electronics system 122.

The parallel hole collimator 112 acts as a guide to channel the gamma rays 110 through the tub 104 to the scintillation crystal 114. The scintillation crystal 114 functions as a gamma ray detector by converting the high-energy photons of the gamma rays 110 into visible light (i.e., lower energy photons). When a gamma ray 110 strikes and is absorbed in the scintillation crystal 114, the energy of the gamma ray 110 is converted into flashes of light 110A (i.e., a large number of scintillation photons) that emanate and spread from the point at which the gamma ray 110 is absorbed. The scintillation crystal 114 may be formed from any suitable materials known in the art, such as sodium iodide doped with a trace of thallium (NaI(Tl)) or CsI(Tl). The scintillation photons 110A emitted from the scintillation crystal 114 are typically in the visible light region of the electromagnetic spectrum (and may have a mean value of about 3 eV for NaI(Tl)).

The light guide 116 assists in focusing the scintillation photons 110A from the scintillation crystal 114 to the PMTs 118. The plurality of PMTs 118 is located adjacent to the light guide 116. In one or more embodiments, the number of PMTs may be on the order of about 50 to 100 tubes arranged in a two dimensional array. The basic function of the PMTs 118 is to detect and amplify the scintillation photons 110A (events).

Each PMT 118 is operable to detect a fraction of the scintillation photons 110A emanating from the scintillation crystal 114 and produce an analog output signal (e.g., a current or voltage pulse) having an amplitude that is proportional to the number of detected scintillation photons 110A. Each PMT 118 includes a light sensitive surface, called the photocathode, which emits electrons in proportion to the number of incident scintillation photons 110A. The emitted electrons, also called photoelectrons, are then electro-statically accelerated into an electron multiplying structure of the PMT 118, which causes an electrical current (or voltage) to be developed at an output of the PMT 118.

The amplitude of the output signal is proportional to the number of photoelectrons generated in the PMT 118 during the time period that scintillation photons 110A are incident. More specifically, the amplitude of the output signal from each PMT 118 is proportional to two basic factors: (i) the number of scintillation photons 110A detected by the PMT 118, and (ii) the gain of the electron multiplying structure of the PMT 118. Thus, after a gamma ray 110 absorption event at the scintillation crystal 114, a given PMT 118 outputs a signal that can be used (with other signals from other PMTs 118) to determine the location of the gamma ray 110 absorption event.

Assuming that the analog output signals from the PMTs 118 are current signals, such output signals are subject to a current-to-voltage conversion to yield an analog voltage signal. The analog voltage signals are then digitalized using analog to digital ("A/D") converters prior to or as an initial stage in the acquisition electronics system 122. The interconnection circuitry 124 communicates the signals from the PMTs 118 to the acquisition electronics system 122.

A basic function of the acquisition electronics system 122 is to calculate the spatial location and energy level of the incident gamma rays 110 based on the digitized analog output signals from the PMTs 118. From such location information, the acquisition electronics system 122 is then operable to produce a two dimensional image of the anatomy of the patient 106, which may be displayed on a CRT or other display mechanism. The number of scintillation photons producing output in each PMT 118 is inversely related to the distance of the PMT 118 from the point of gamma ray absorption, or event location, within the scintillation crystal 114. Thus, the acquisition electronics system 122 uses this relationship to compute the position of the gamma event from the output signals of a number of the PMTs 118 surrounding the event location.

Further details regarding the basic operation and structure of the gamma ray detection circuitry of the SPECT scanner 100 may be found in U.S. Patent Application Publication No. US2004/0036026 and/or U.S. Pat. No. 6,124,595, the entire disclosures of which are hereby incorporated by reference.

Figure 3A:
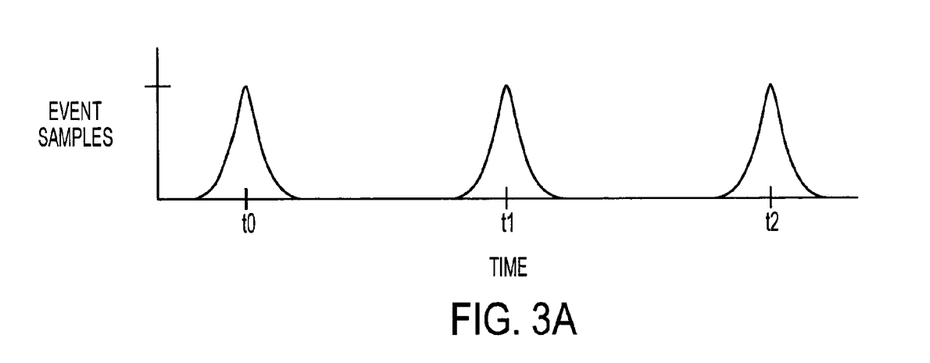
FIG. 3A is graphical illustration of one or more output signals from the photo multiplier tube(s) of the gamma ray detection circuitry of the SPECT scanner in response to incident gamma rays.
Figure 3B:
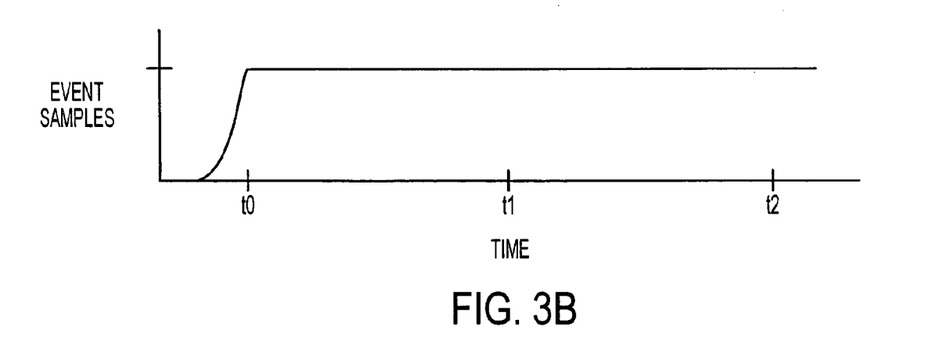
FIG. 3B is graphical illustration of one or more output signals from the photo multiplier tube(s) of the gamma ray detection circuitry of the SPECT scanner in response to incident X-rays.

Referring to FIGS. 3A and 3B, two graphical illustrations depict typical output signals from the photo multiplier tubes 118 of the SPECT scanner 100 in response to incident gamma rays (FIG. 3A) and incident X-rays (FIG. 3B). In the context of the gamma rays 110 and X-rays 108 discussed herein, it is assumed that the energy profile of a gamma ray event exhibits a generally Gaussian envelope, as is illustrated in FIG. 3A. The illustrated envelope may represent a number of digitized event samples from the PMTs 118 (post A/D conversion). In a typical SPECT scanning situation, gamma ray events are somewhat random and the Gaussian profile of a given gamma ray event peaks and returns to zero in a time period of about 1 us. In contrast, as shown in FIG. 3B, the X-rays 108 of the CT scanner are produced via electron acceleration and therefore have a much greater energy profile in terms of duration (much greater than 1 us) and often also in terms of amplitude.

As discussed above, location of the CT scanner 102 in close proximity to the SPECT scanner 100 may subject the gamma ray detection circuitry of the SPECT scanner 100 to X-rays of significant magnitude. Given the significantly greater energy profile of the X-rays 108, the output of the SPECT scanner 100 may be skewed due to overdriving of the scintillation crystal 114 and the PMTs 118. Assuming that these components are not damaged, it may take a very long time (sometimes hours) for one or both of the scintillation crystal 114 and the PMTs 118 to settle and again become useful in measuring gamma rays 110. Hence the need for the lead tub 104 to block as much incident X-ray radiation as possible.

Figure 4:
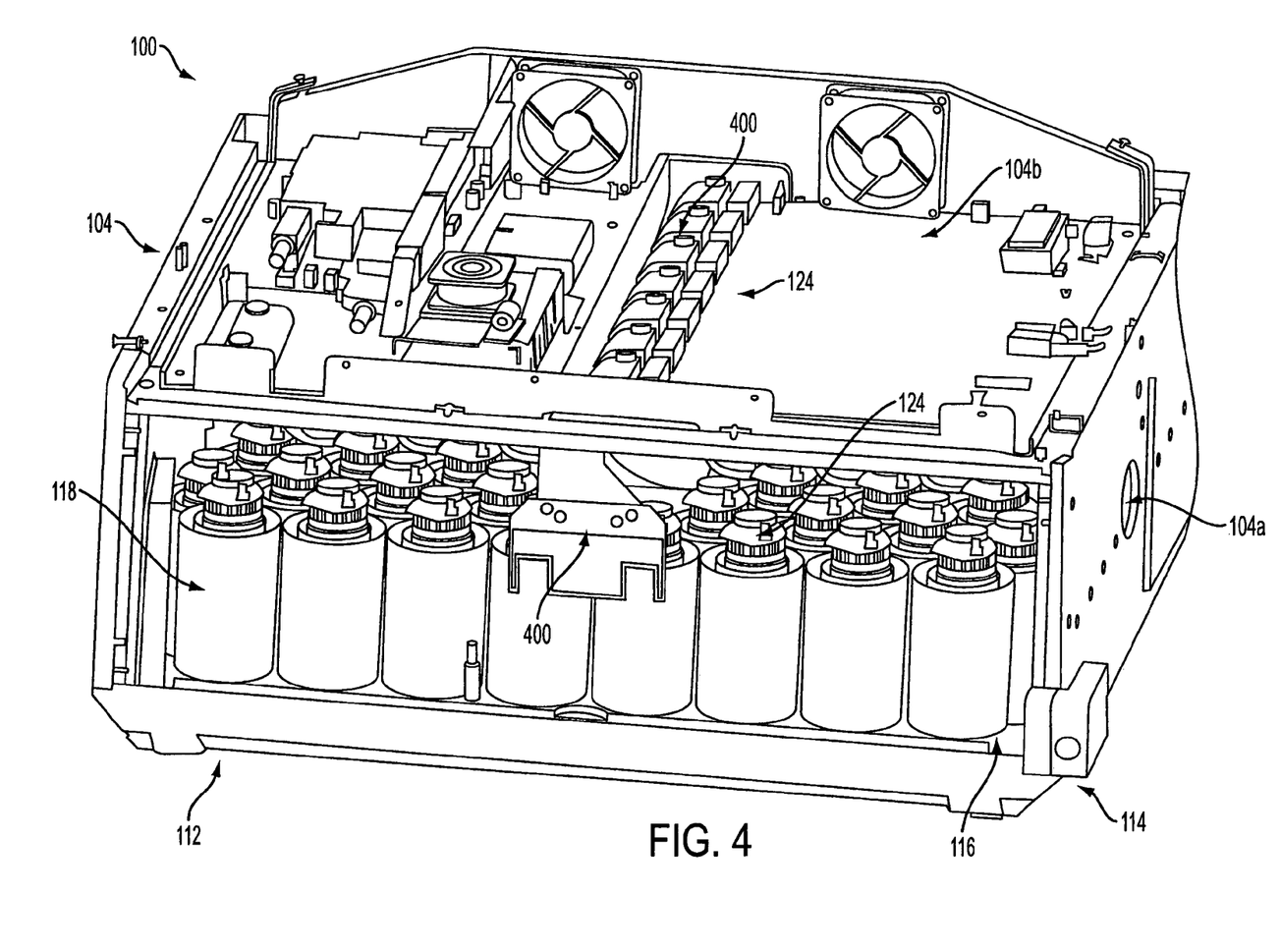
FIG. 4 is a partial sectional perspective view of an exemplary electrical penetration assembly interconnected with an array of PMTs residing within a tub in accordance with one or more embodiments of the present invention.

Referring to FIG. 4, a partial sectional perspective view of an exemplary electrical penetration assembly 400 interconnected with an array of PMTs 118 residing within a tub 104 is shown in accordance with one or more embodiments of the present invention. These components are depicted in the context of a nuclear detector 100, such as a SPECT scanner. The tub 104 is shown with the sides 104a removed so that the contents of the tub 104 are visible. A top 104b of tub 104, though, is shown, through which the electrical penetration assembly 400 penetrates.

The interconnection circuitry 124 necessarily resides, in large part, within the tub 104, insofar as the PMTs 118 reside within the tub 104. However, as discussed above, portions of the acquisition electronics system 122 historically also have been packaged inside the tub 104 due to the large number of connections to the PMTs 118. According the present invention, however, as shown in FIG. 2, the acquisition electronics system 122 may be located outside the tub 104 due to the interconnection circuitry 124 that consolidates all the necessary connections in an electrical penetration assembly 400.

As depicted in further detail in FIGS. 5-8, electrical penetration assembly 400 organizes the interconnection circuitry 124 and passes it through the top 104b of the tub 104. Moreover, the electrical penetration assembly 400 may prevent light from entering the tub 104 where the interconnection circuitry 124 traverses the top 104b, thereby creating a light seal. In contrast to the prior art, the light seal may be (1) integrated with the tub, (2) reusable, (3) easily assembled, and (4) easily disassembled. An added advantage may exist where the electrical penetration assembly 400 may include components made of plastic, or other insulators, inasmuch as the electrical penetration assembly 400 may provide an extra dielectric layer of insulation for additional protection of the high voltage traces of the interconnection circuitry 124.

Figure 5:
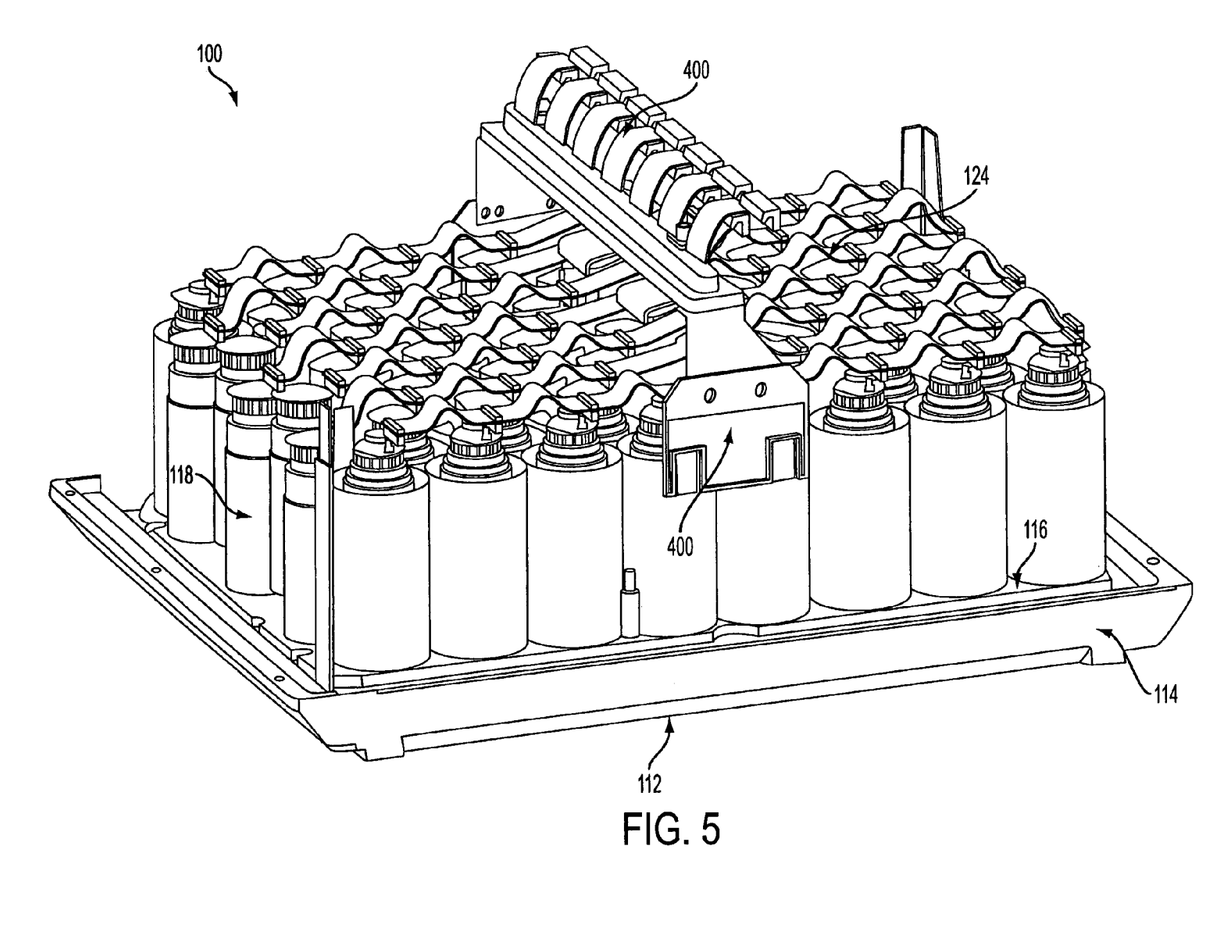
FIG. 5 is a perspective view of an exemplary electrical penetration assembly interconnected with an array of PMTs in accordance with one or more embodiments of the present invention.

Referring to FIG. 5, a perspective view of an exemplary electrical penetration assembly interconnected with an array of PMTs is shown in accordance with one or more embodiments of the present invention. These components also are depicted in the context of a nuclear detector 100, similar to that shown in FIG. 4. Much of the nuclear detector 100, though, has been removed to reveal the electrical penetration assembly 400 and its position relative to the PMTs 118. In the present embodiment, the nuclear detector 100 includes 59 PMTs 118, arranged in offset rows having the pattern of 8-9-8-9-8-9-8. The rows may be offset to conserve space, but any arrangement or number of PMTs is conceivable.

Figure 6:
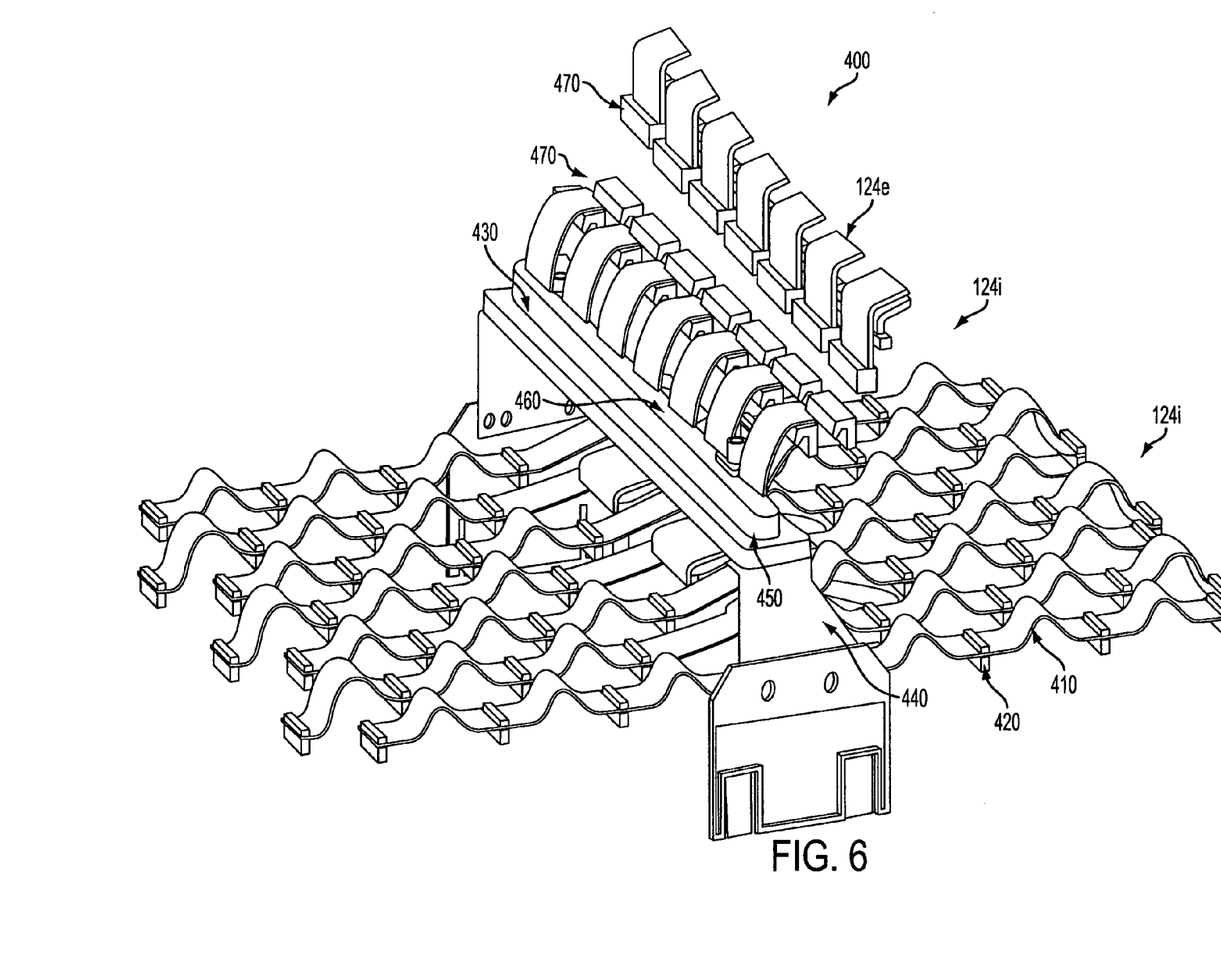
FIG. 6 is a perspective view of an exemplary electrical penetration assembly in accordance with one or more embodiments of the present invention.

Referring to FIG. 6, a perspective view of an exemplary electrical penetration assembly 400 is shown in accordance with one or more embodiments of the present invention. An exemplary embodiment of the electrical penetration assembly 400 may include flex circuits 410, flex circuit-PMT connectors 420, a flex circuit guide 430, a tub-penetration mechanical support 440, a support-to-tub retention mechanism 450, and a light seal 460.

In the context of the interconnection circuitry 124 used to connect the PMTs 118 to the power supply 120 and the acquisition electronics system 122, interconnection refers to the networking of the acquisition electronics system 122 with the individual PMTs 118, such as in a hub-and-spoke configuration of electrical connections. Each PMT 118 needs to have an independent data connection to the acquisition electronics system 122, in order for the acquisition electronics system 122 to calculate scintillation positions relative to the spatial configuration of the PMTs 118.

However, the PMTs 118 may themselves be electrically interconnected, inasmuch as the PMTs 118 may share circuitry, such as common power and ground connections. The interconnection circuitry 124 shown in FIG. 6 reflects such an electrical interconnection of PMTs 118. Electrically interconnecting the PMTs 118 to share circuitry may be done to reduce the number of circuits, and possibly thus reducing cost and conserving space, but it may reduce reliability to the extent that circuitry redundancy is reduced. For instance, if a shared power circuit fails, all electrically interconnected PMTs 118 will fail too. If the reduction in reliability is minimal, though, in comparison to the reduction in costs, electrically interconnecting PMTs 118 as in FIG. 6 may be preferable.

Additionally, or alternatively, the PMTs 118 may be physically interconnected, but not electrically, if circuitry to the physically interconnected PMTs 118 is bundled but not shared. Bundling of circuitry may be done to conserve space and organize otherwise loose circuits, but, depending on how it is done, bundling may also complicate the assembly and disassembly of individual PMTs 118. Nonetheless, bundling may be preferable if the advantage outweigh the disadvantages of a given arrangement.

Figure 7:
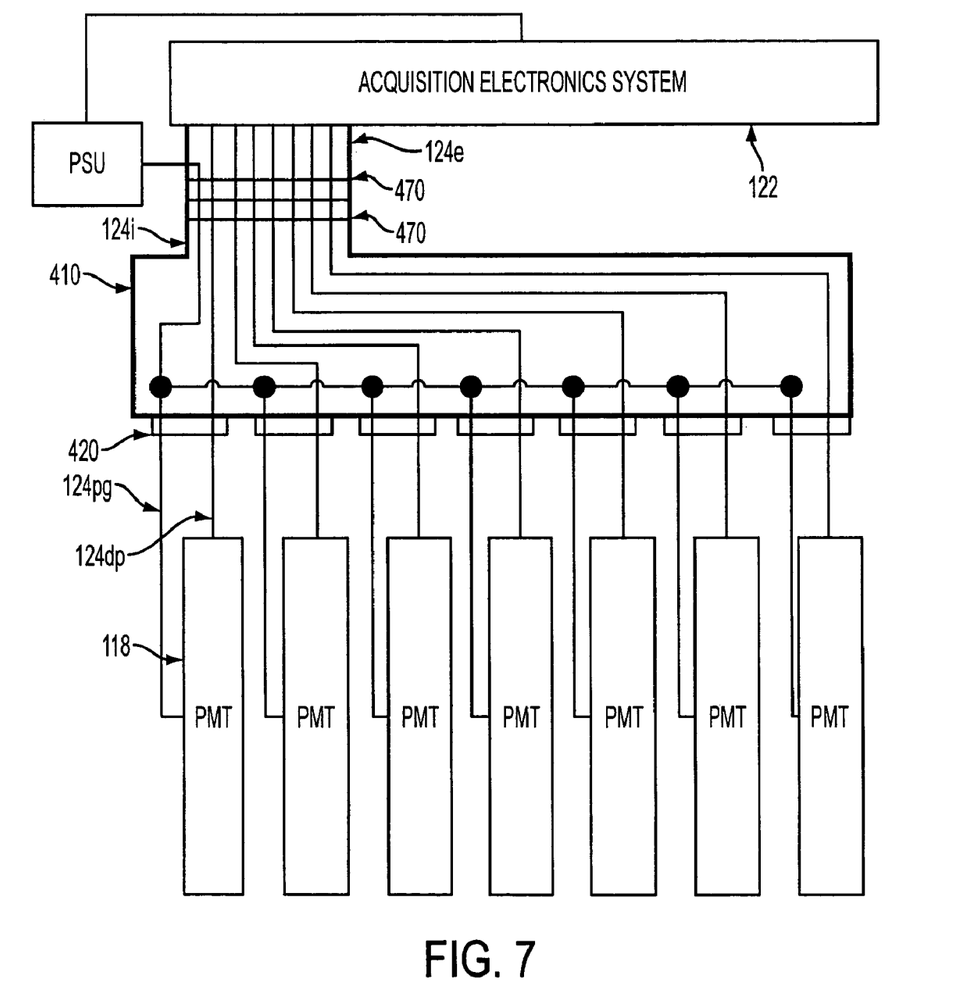
FIG. 7 is a simplified block diagram of interconnection circuitry within a flex circuit in accordance with one or more embodiments of the present invention.

Referring to FIG. 7, a simplified block diagram of interconnection circuitry 124 is depicted within a flex circuit 410 according to an exemplary embodiment of the present invention. As depicted the diagram of in FIG. 7, and shown in FIGS. 4-6, the interconnection circuitry 124 of the PMTs 118 may be both physically and electrically interconnected using flex circuits 410 that both bundle the individual differential pairs 124dp for each PMT 118, and share the power and ground circuits 124pg between the PMTs 118. Using one flex circuit 410 for four PMTs reduces the potential number of flex circuits 410, as well as the associated clutter and costs, likewise by a factor of four. The arrangement shown in FIG. 7 represents an exemplary high-density configuration of interconnection circuitry 124.

Although preferred, it is not necessary to either physically or electrically interconnect the PMTs 118 with each other. For instance, each PMT 118 could have its own flex circuit 410 having its individual differential pair 124dp and individual power and ground circuits 124pg. Such a low-density arrangement would require many more flex circuits 410, and the flex guide 430 and light seal 460 would need to accommodate the additional flex circuits 410 penetrating the tub 104.

The flex circuits 410 use a technology for building electronic circuits called flexible electronics, in which electronic devices are deposited on flexible substrates such as plastic. In the simplest case, flexible electronics can be made by using many of the same components used for rigid printed circuit boards, with exception of the substrate, being made flexible, rather than rigid. Flex circuits are often used for connections in various applications where flexibility, space savings, or production constraints limit the serviceability of rigid circuit boards or hand wiring. In addition to cameras, a common application of flex circuits is in computer keyboard manufacturing; most keyboards made today use flex circuits for the switch matrix.

The flex circuits 410 comprise an interior portion 124i of the interconnection circuitry 124, i.e., within the tub 104. In order to complete the connection to the acquisition electronic system (AES) 122, an exterior portion 124e of the interconnection circuitry 124, i.e., outside of the tub 104, needs to connect to the flex circuits 410 via flex circuit-AES connectors 470 and extend from the nuclear detector 100 to the AES 122. The exterior portion 124e also may use flexible electronics.

In an exemplary embodiment shown, 14 flex circuits 410 interconnect the 59 PMTs 118, with each flex circuit 410 servicing either 4 or 5 PMTs 118. Insofar as each PMT 118 requires several circuits for its various functions, such as circuits for power, ground, differential pairs, etc., each flex circuit 410 has dozens of pin lines and acts as a means of high-density interconnection with the interconnection circuitry 124.

The flex circuits 410 connect to the PMTs 118 via the flex circuit-PMT connectors 420, rise up through the flex circuit guide 430, and are held in place when the flex circuit guide 430 and light seal 460 are assembled and retained in place using the support-to-tub retention mechanism 450, which attaches to the tub-penetration mechanical support 440. The flex circuit guide 430 may act as means of routing the high-density interconnection, whereas the tub-penetration mechanical support 440 may act as means of stable support of the high-density interconnection.

Figure 8:
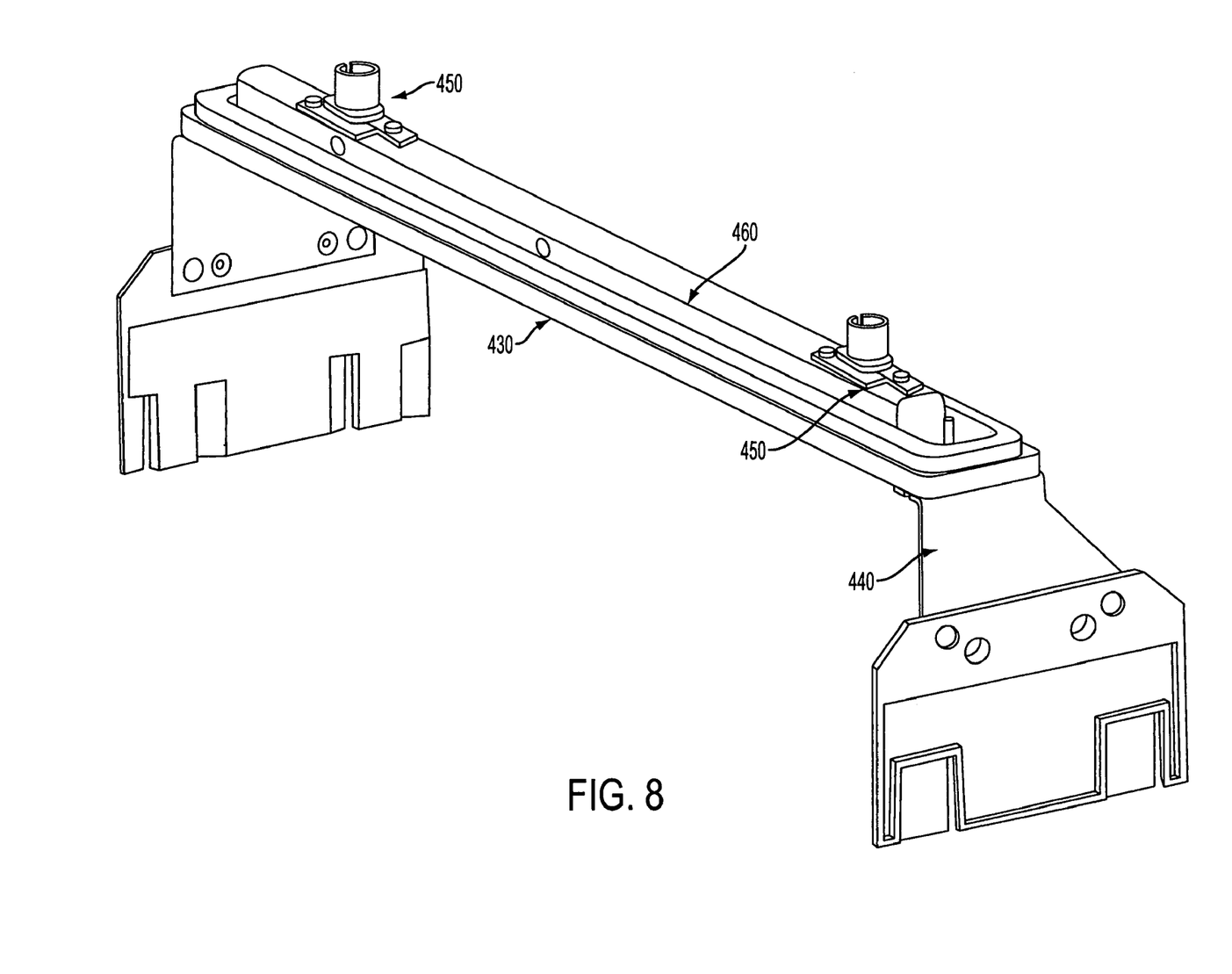
FIG. 8 is a perspective view of an exemplary mechanical support in accordance with one or more embodiments of the present invention.

Referring to FIG. 8, a perspective view of an exemplary mechanical support 440 is shown in accordance with one or more embodiments of the present invention. With the mechanical support 440 are shown in assembled form the flex circuit guide 430, the support-to-tub retention mechanism 450 and the light seal 460. Considering that FIG. 8 does not depict the flex circuits 410, it is easier to see that the flex circuit guide 430 and light seal 460 effectively block out all light when assembled and fastened together.

Figure 9:
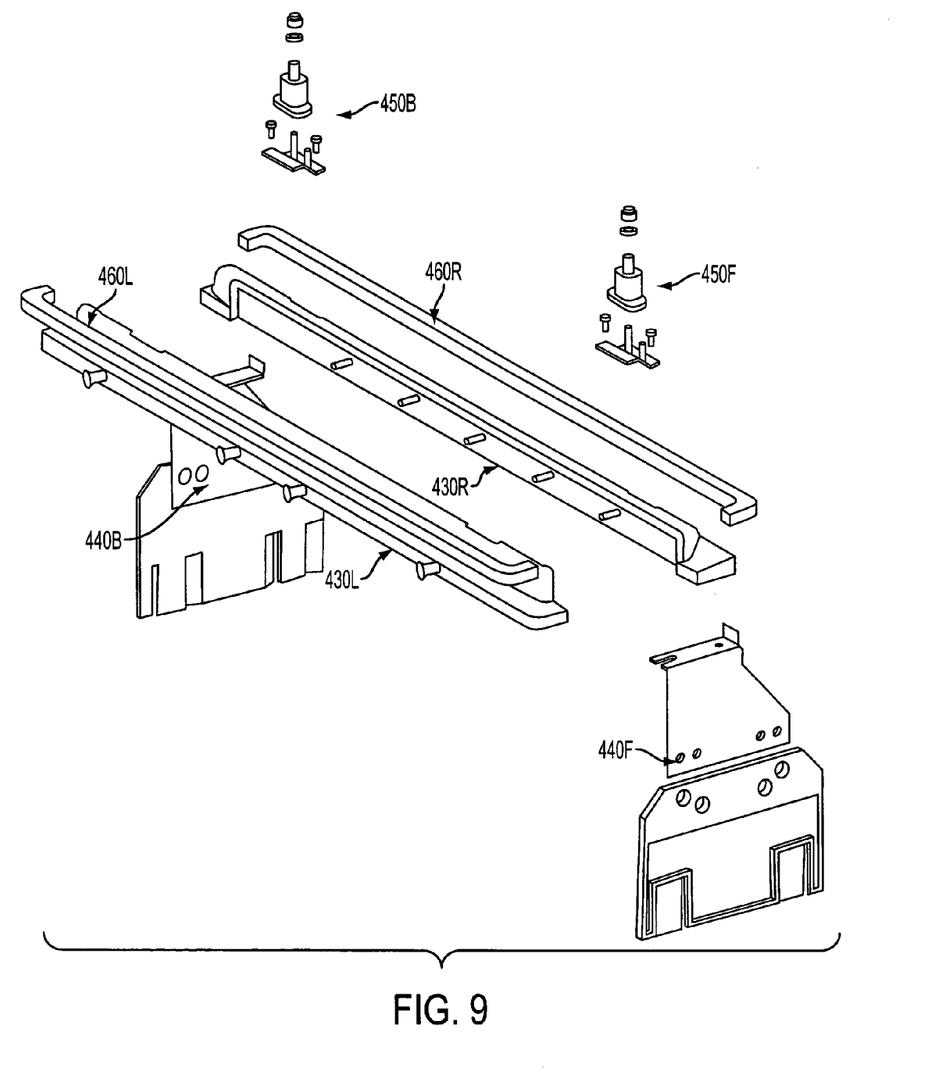
FIG. 9 is a perspective view of an exploded exemplary mechanical support in accordance with one or more embodiments of the present invention.

Referring to FIG. 9, a perspective view of an exploded exemplary mechanical support 440 is shown in accordance with one or more embodiments of the present invention. As in FIG. 8, with the mechanical support 440 are shown in exploded form the flex circuit guide 430, the support-to-tub retention mechanism 450 and the light seal 460. As shown in FIGS. 4-6, the flex circuits 410 would rise up between the left and right sides 430L, 430R of the flex circuit guide 430 and between the left and right sides 460L, 460R of the light seal 460. The front and back fasteners 450F, 450B of support-to-tub retention mechanism 450 serve to fasten the flex circuit sides 430L, 430R and the light seal sides 460L, 460R together and retain them against the front and back portions 440F, 440B of the mechanical support 440.

Figure 10:
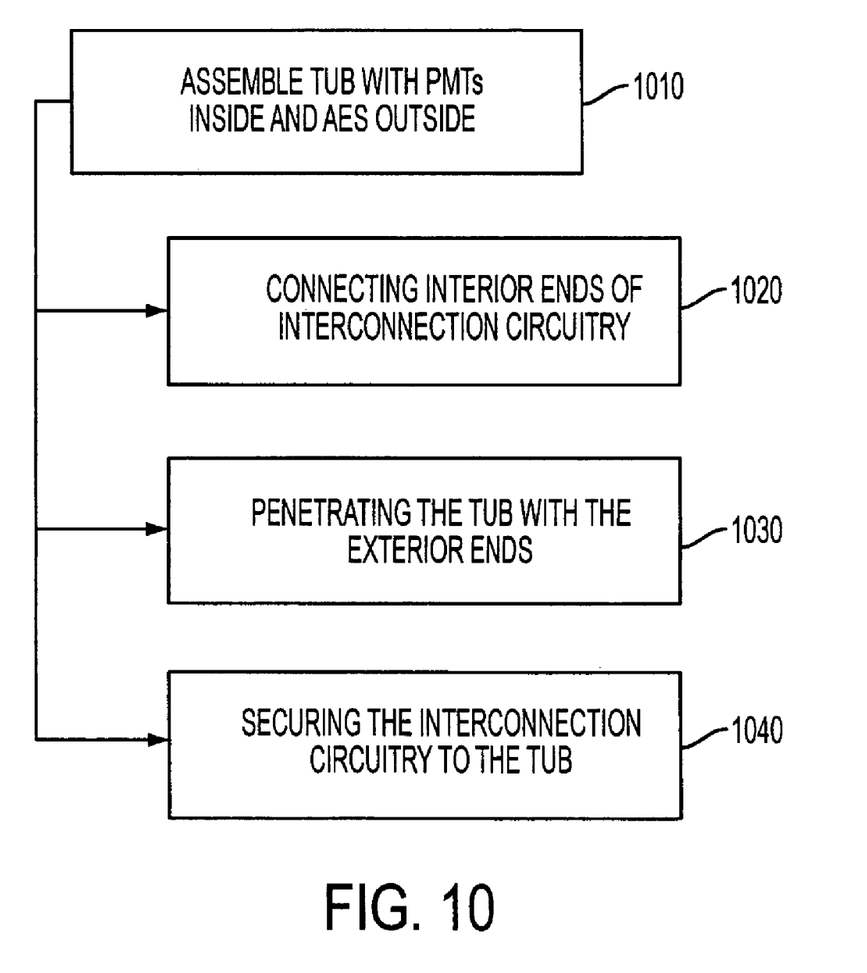
FIG. 10 is a flow diagram illustrating actions of assembling a tub, in implementing exemplary embodiments of the present invention.
Figure 11:
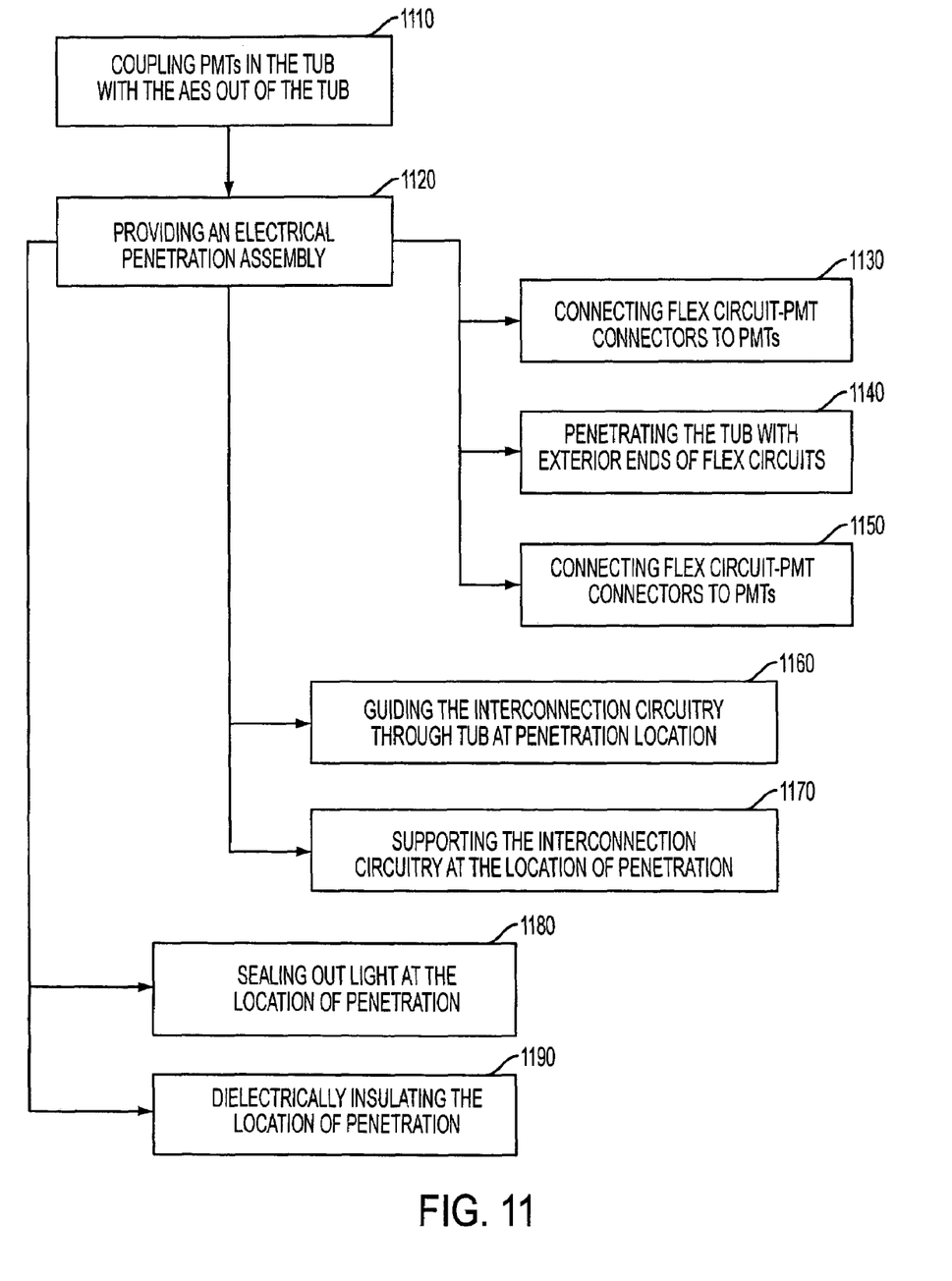
FIG. 11 is a flow diagram illustrating actions of coupling PMTs inside of a tub with an acquisition electronics system outside of the tub, in implementing exemplary embodiments of the present invention.

Reference is now made to FIGS. 10 and 11, which are flow diagrams illustrating process actions that may be carried out in implementing exemplary embodiments of the present invention. The illustrated actions, identified with parenthetical references, are examples only and are not intended to limit the invention, nor indicate a particular sequence of events. Various combinations of the actions are conceivable, as are various sequences of the actions, and all of these are considered within the scope of the present invention.

Referring to FIG. 10, a method of assembling (1010) a tub 104 of a nuclear detector 100 may include connecting (1020) interior ends 124i of interconnection circuitry 124 to PMTs 118, penetrating (1030) the tub 104 with exterior ends 124e of the interconnection circuitry 124, and securing (1040) the interconnection circuitry 124 to the tub 104 where the interconnection circuitry 124 penetrates the tub 104.

Referring to FIG. 11, a method of coupling (1110) a plurality of PMTs 118 inside of a tub 104 with an acquisition electronics system 122 outside of the tub 104 may include providing (1120) an electrical penetration assembly 400 between the plurality of PMTs 118 and the acquisition electronics system 122. Providing (1120) the electrical penetration assembly 400 may include connecting (1130) flex circuit-PMT connectors 420 at interior ends 124i of flex circuits 410 to the plurality of PMTs 118, penetrating (1140) the tub 104 with exterior ends 124e of the flex circuits 410; and connecting (1150) the flex circuit-AES connectors 470 at exterior ends 124e to the acquisition electronics system 122. Providing the electrical penetration assembly 400 also may include guiding (1160) the interconnection circuitry 124 through the tub 104 at a location of penetration, and supporting (1170) the interconnection circuitry 124 at the location of penetration of the tub 104. Providing the electrical penetration assembly 400 also may include sealing out (1180) light from the tub enclosure at a location of penetration of the tub enclosure, and dielectrically insulating (1190) the location of penetration of the tub 104.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A method of assembling a tub enclosure of a nuclear detector, the method comprising:
   connecting interior ends of interconnection circuitry to a plurality of photo-multiplier tubes (PMTs) inside of the tub enclosure of the nuclear detector;
   penetrating the tub enclosure with exterior ends of the interconnection circuitry; and
   securing the interconnection circuitry to the tub enclosure where the interconnection circuitry penetrates the tub enclosure;
   wherein the exterior ends of the interconnection circuitry are configured to couple with an acquisition electronics system outside of the tub enclosure.

2. A method of coupling a plurality of photo-multiplier tubes (PMTS) inside of a tub enclosure of a nuclear detector with an acquisition electronics system outside of the tub enclosure, the method comprising:
   providing an electrical penetration assembly between the plurality of PMTs and the acquisition electronics system;
   wherein the electrical penetration assembly allows interconnection circuitry coupling the plurality of PMTs and the acquisition electronics system to penetrate the tub enclosure.

3. The method of claim 2, wherein the providing an electrical penetration assembly comprises:
   connecting interior ends of flex circuits to the plurality of PMTS;
   penetrating the tub enclosure with exterior ends of the flex circuits; and
   connecting the exterior ends to the acquisition electronics system.

4. The method of claim 2, wherein the providing an electrical penetration assembly comprises:
   guiding the interconnection circuitry through the tub enclosure; and,
   supporting the interconnection circuitry at a location of penetration of the tub enclosure.

5. The method of claim 2, wherein the providing an electrical penetration assembly comprises:
   sealing out light from the tub enclosure at a location of penetration of the tub enclosure; and,
   insulating dielectrically the location of penetration of the tub enclosure.

6. An apparatus, comprising an electrical penetration assembly for use with a tub enclosure of a nuclear detector,
   wherein the electrical penetration assembly penetrates the tub enclosure with electrical connections between a plurality of photo-multiplier tubes (PMTs) encased within the tub enclosure and an acquisition electronics system (AES) residing outside the tub enclosure, and an acquisition electronics system (AES) residing outside the tub enclosure.

7. The apparatus of claim 6, wherein the nuclear detector comprises a single photon emission computed tomography (SPECT) scanner.

8. The apparatus of claim 6, wherein the electrical penetration assembly further comprises:
   a tub-penetration mechanical support;
   a support-to-tub retention mechanism; and,
   a light seal.

9. The apparatus of claim 6, wherein the electrical penetration assembly comprises:
   at least one flex circuit;
   a plurality of flex circuit-PMT connectors; and,
   a flex circuit guide.

10. The apparatus of claim 9, wherein the electrical penetration assembly further comprises:
    at least one flex circuit-AES connector.

11. An nuclear detector system comprising:
    a plurality of photo-multiplier tubes (PMTs);
    a tub enclosure encasing the plurality of PMTs;
    an acquisition electronics system (AES) residing outside the tub enclosure;
    interconnection circuitry coupling the plurality of PMTs with the acquisition electronics system; and
    an electrical penetration assembly;
    wherein the electrical penetration assembly penetrates the tub enclosure with the interconnection circuitry and electrically connects the interconnection circuitry to the plurality of PMTs.

12. The system of claim 11, wherein the electrical penetration assembly further comprises:
    a tub-penetration mechanical support;
    a support-to-tub retention mechanism; and,
    a light seal.

13. The system of claim 11, wherein the electrical penetration assembly comprises:
- at least one flex circuit;
- a plurality of flex circuit-PMT connectors; and,
- a flex circuit guide.

14. The system of claim 13, wherein the electrical penetration assembly further comprises:
- at least one flex circuit-AES connector.

15. An apparatus, comprising:
- means for electrically connecting a plurality of photo-multiplier tubes (PMTs) inside of a tub enclosure of a nuclear detector and an acquisition electronics system outside of the tub enclosure; and
- means for penetrating the tub enclosure with the interconnection circuitry.

16. The apparatus of claim 15, further comprising:
means for sealing out light;
wherein the means for sealing out light prevents light from entering the tub enclosure where the interconnection circuitry penetrates the tub enclosure.

17. The apparatus of claim 15, further comprising:
means for mechanically supporting the means for penetrating the tub enclosure with the interconnection circuitry.

18. The apparatus of claim 15, further comprising:
means for dielectrically insulating the means for electrically connecting a plurality of PMTs.

19. The apparatus of claim 15:
wherein the means for electrically connecting includes means for electrically interconnecting the plurality of PMTs.

20. The apparatus of claim 19:
wherein the means for electrically interconnecting the plurality of PMTs includes a high-density configuration of interconnection circuitry.

* * * * *